(12) United States Patent  
Wechtenhiser

(10) Patent No.: US 8,643,478 B2
(45) Date of Patent: Feb. 4, 2014

(54) MOUTH PIPE UNIT FOR ACTIVATING A DEVICE

(76) Inventor: Bert W. Wechtenhiser, Jacksonville, FL (US)

( * ) Notice: Subject to any disclaimer, the term of this patent is extended or adjusted under 35 U.S.C. 154(b) by 235 days.

(21) Appl. No.: 13/200,293

(22) Filed: Sep. 21, 2011

(65) Prior Publication Data

US 2013/0069770 A1     Mar. 21, 2013

(51) Int. Cl.
*G08B 5/22*        (2006.01)
(52) U.S. Cl.
USPC ....................................................... 340/286.07
(58) Field of Classification Search
USPC ............... 340/286.07, 573.1, 286.06, 506, 340/539.12; 341/21, 34
See application file for complete search history.

(56) References Cited

U.S. PATENT DOCUMENTS

| | | | |
|---|---|---|---|
| 2,805,379 A | 9/1957 | Troeller et al. | |
| 3,731,025 A | 5/1973 | Filliung | |
| 4,298,863 A * | 11/1981 | Natitus et al. | 340/573.1 |
| 4,706,067 A | 11/1987 | Hauck | |
| 5,126,731 A * | 6/1992 | Cromer, Jr. | 340/4.11 |
| 5,365,026 A | 11/1994 | Cromer, Jr. et al. | |
| 6,801,231 B1 * | 10/2004 | Beltz | 715/865 |
| 6,833,786 B1 * | 12/2004 | Sun et al. | 340/539.12 |
| 2003/0216660 A1 | 11/2003 | Ben-Oren et al. | |
| 2005/0007223 A1 | 1/2005 | Schulze | |
| 2009/0264006 A1 | 10/2009 | Silkey et al. | |

* cited by examiner

*Primary Examiner* — Phung Nguyen
(74) *Attorney, Agent, or Firm* — Paul Bogdon

(57) ABSTRACT

A mouth pipe and porous filter unit for operation of a device, e.g. a pneumatically actuated device, comprises a mouth pipe in communication with an air tube for delivering blown air to the device. The mouth pipe comprises a one-piece transparent thermoplastic extrusion member and has an integral projection for grasping the mouth pipe. The porous filter has a pore size ranging from 90 microns to 130 microns for preventing saliva and/or blood of a patient from flowing into the air tube and surrounding environment. The mouth pipe comprises a first diameter section, a transition member, and an enlarged second diameter section which form a continuous airway therein and the porous filter is wedged within the enlarged second diameter section of the mouth pipe. The material of the mouth pipe may be polyvinyl chloride, and the material of the filter may be polystyrene.

15 Claims, 2 Drawing Sheets

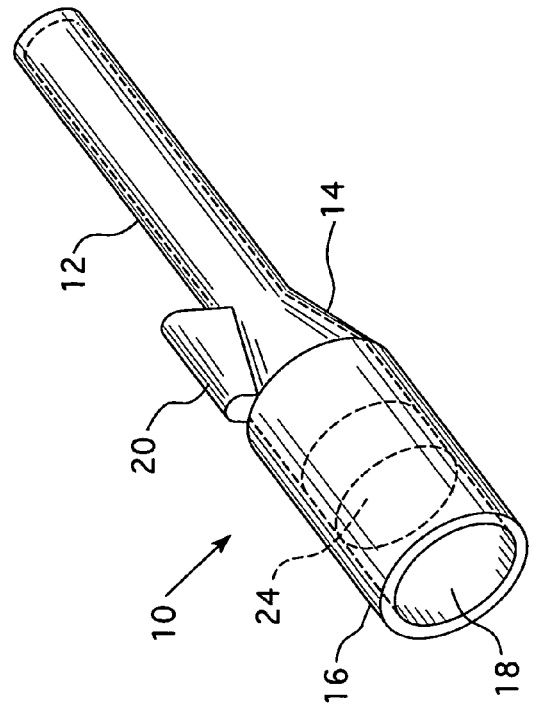
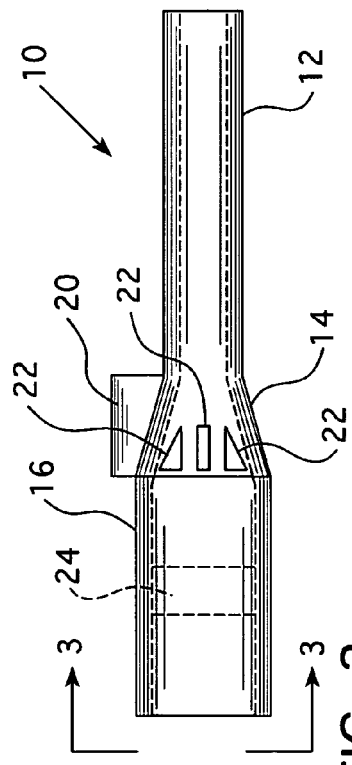
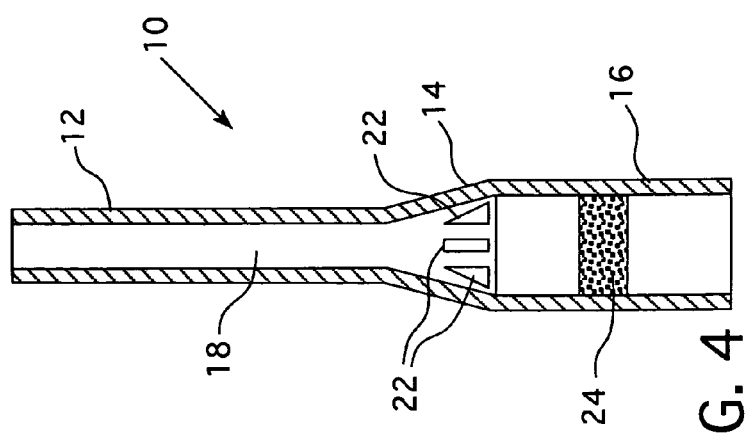
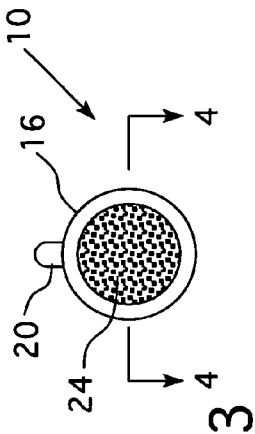

MOUTH PIPE UNIT FOR ACTIVATING A DEVICE

BACKGROUND OF THE INVENTION

1. Field of the Invention

The present invention relates to a breath controlled device and more particularly to a mouth pipe unit used to deliver air to activate a device, such as, a pneumatically operated switching device for sending an electrical signal to a nurse's station for assistance.

2. Description of the Prior Art

It is known in the art to use pneumatically actuated switches rather than electrical switches as part of nurse call systems. Such switches, disclosed for example in U.S. Pat. No. 3,823,285 to Dwyer, are particularly beneficial where combustion concerns may be present, as in oxygen rich environments, in that the construction of the pneumatically actuated switching device limits the possibility of arcing which is generally a problem associated with electrical switches.

The above U.S. Pat. No. 3,823,285 illustrates an example of a pneumatically actuated bulb device for a patient actuated nurse call system. This device includes a deformable pneumatic bulb which a patient compresses in order to provide pressurized air to operate an electrical switching circuit that is well suited for use in environments where it is undesirable to use a conventional electrical switch as discussed in the preceding paragraph.

A patient actuated call system is not only commonly used in hospital rooms but also in other health care facilities where there is a need to summon personnel for help, particularly, when a patient is in a weakened or disabled condition. Most hospitals and health care institutions have signaling systems in each patient area in which a patient may initiate a signal that is received at a station or an allocated substation within a larger area to summon assistance. Typically, for example in a hospital, a select group of patient areas is serviced by a given nurse station where calls for assistance by patients are taken. Most patient areas must accommodate the use of oxygen even if only on an emergency basis whereby electrical switches commonly used in other industries cannot be utilized. The pneumatically actuated device disclosed in the aforesaid U.S. Pat. No. 3,823,285 provides an entirely satisfactory solution to the need for a pneumatically activated switching device which can operate in a very reliable fashion in hostile environments particularly atmospheres containing a high concentration of oxygen that could otherwise cause combustion. In this device, a deformable bulb operated by the patient supplies pneumatic pressure to the substation for assistance.

A further development of a pressurizing device is disclosed in U.S. Pat. No. 5,155,309 to Dwyer which embodies a pneumatic bulb with an actuator dome resembling a doughnut to provide a distinctive identification to the bulb from other pneumatic bulbs that may be used for different purposes in a patient area. A base plate includes protruding truncated conical members which act to maintain the doughnut shaped actuator at a fixed location on a patient's bed so that the patient can compress the bulb to summon help. That is, this device is also operated by the patient pushing down on a pneumatic bulb for delivering pressurized air to an electrical switch.

Further examples of well-known nurse call systems can be found in U.S. Pat. Nos. 3,781,843 to Harrison, et al; 4,298,863 to Natitus et al; 4,484,367 to Jenkins; and 4,702,443 to Callaway. U.S. Pat. No. 3,781,843 discloses a bed guard system having restraining rails fitted with a detector. The detector is formed with an elongated rail engaging pocket shaped to fit on the rail and an overlying elongated internal cavity extending the length of the rail. The internal cavity forms a site for a fluid material which can be pressurized by an applied pressure to the top surface of the rail covering. U.S. Pat. No. 4,298,863 discloses a patient call system in which a patient operated transducer, mounted on a patient's face or a section of the body, is interconnected by pneumatic tubing to a pneumatically actuated switch that is part of an electronic monitoring system. In U.S. Pat. No. 4,484,367, a side rail of a patient's bed is wrapped with a flexible sheet having a pocket for receiving an electronic push button device serving as a call device for summoning a nurse. In U.S. Pat. No. 4,702,443, a cord holding device is disclosed wherein a holding member supports a cord to allow limited movement of the cord, the end of which carries a push button electric switch.

Several well-known pneumatically actuated patient call systems, such as those discussed herein above, are manually operated by the patient who pushes down onto a pneumatic actuator for creating and delivering pressurized air to a switching device which operates to general an electrical signal in a nurse's station for assistance.

In some cases, the patient may be physically challenged or unable to manually operate a device. In this instance, the patient may need to blow into a mouth piece for delivering the required air for triggering a device. Examples of such devices are disclosed in U.S. Pat. Nos. 5,126,731 to Cromer, Jr. et al and 5,365,026 to Cromer, Jr. et al.

U.S. Pat. No. 5,126,731 discloses a pneumatically controlled, user-operated switch interface which allows a physically disabled person to operate electronic equipment such as a computer, television, a video cassette recorder and a remote control includes an apparatus providing an airway passage, first switching circuitry for producing a plurality of switching signals and having a pneumatic switch responsive to air pressure in an airway passage. A mouthpiece 10 is used for delivering high and low air pressure and has an internal wet cotton filter which collects saliva and entraps harmful bacteria during use of the switch interface.

U.S. Pat. No. 5,365,026 discloses a user interface controller for use by physically challenged persons having multiple function capabilities to operate an electronic device such as a computer or video game system. The controller provides activation of a plurality of first type control devices through a first type movement of a mouthpiece actuator and activation of one or more second control devices within a selected bank of control devices through puff and sip operations performed through a mouthpiece which includes a moisture filter.

There is a need to provide a mouth pipe unit comprising a porous filter for operation of a breath controlled device, and which mouth pipe unit is relatively simple and inexpensive to produce, is replaceable and disposable for sanitation purposes; and wherein a plurality of mouth pipe units can be packaged and sold.

SUMMARY OF THE INVENTION

The invention has met this need. The present invention optionally relates to an air actuated devices, such as, for example, a pneumatically actuated switching device in a patient call system which is breath controlled and which invention provides a mouth pipe unit comprising a mouth pipe and a porous filter for such device. The mouth pipe is structured to be connected to an air tube for delivering air pressure to activate a switch to generate an electrical signal to operate the device, e.g. an alarm in a nurse's station. In an embodiment of the invention, the mouth pipe is a one-piece transparent thermoplastic extrusion member having an integral projection for grasping or clutching the mouth pipe. This integral projection may assist in the mouth pipe being easily connected to the air tube by nurse personnel; or if the patient has limited manual dexterity or is physically challenged, the integral projection may assist in the patient's ability to hold the mouth pipe for operation of the device. The mouth pipe comprises a first diameter section, a tapered transition section, and an enlarged second diameter section which is in communication with the tapered transition section and the first diameter section and which three sections form a continuous airway. The enlarged second diameter section of the mouth pipe is wedged into a vented open end of a connector member which retains the air tube. The mouth pipe receives blown air from the user and delivers this air into the air tube for operation of the pneumatically actuated switching device.

The mouth pipe includes a porous filter which fits, preferably in a wedged-like manner, into the enlarged second diameter section of the mouth pipe and which porous filter aids in preventing bodily fluids, e.g. saliva and/or blood of a patient from flowing into the air tube. The mouth pipe may be comprised of a soft thermoplastic material, such as, for example, PVC (polyvinyl chloride). The porous filter may be comprised of a relatively rigid material, such as, for example, polystyrene. The filter may have a pore size ranging from about 90 microns to about 130 microns, and preferably is about 90 microns. The porous filter in general is a relatively small disc having a diameter ranging from about 3/4 inch to about 3/4 inch, preferably about 1/4 inch and a thickness ranging from about 3/16 to about 6/16 inch, preferably about 4/16 inch, depending on the dimensions of the mouth pipe 10.

The mouth pipe and porous filter are designed such that they can be mass produced and sold as a unit. A plurality of such units can be packaged and sold. Producing these units is expected to be inexpensive; and therefore, the mouth pipe and porous filter can be discarded as a unit and easily replaced with another mouth pipe and porous filter unit.

It is therefore an object of the present invention to provide a mouth pipe and porous filter unit for use in breath controlled device, and which unit is made of relatively inexpensive materials, is relatively inexpensive to produce, and which unit is intended to be discarded after one or a couple of uses and which is easily replaced with another mouth pipe and filter unit.

These and other objects of the invention will be better appreciated and understood when read in light of the accompanying drawings.

BRIEF DESCRIPTION OF THE DRAWINGS

FIG. 1 is a perspective view of the mouth pipe unit of the invention.

FIG. 2 is a right side elevation view of the mouth pipe unit of FIG. 1.

FIG. 3 is a view taken along lines 3-3 of FIG. 2.

FIG. 4 is a cross-sectional view taken along lines 4-4 of FIG. 3.

DETAILED DESCRIPTION OF THE INVENTION

Figure 5:
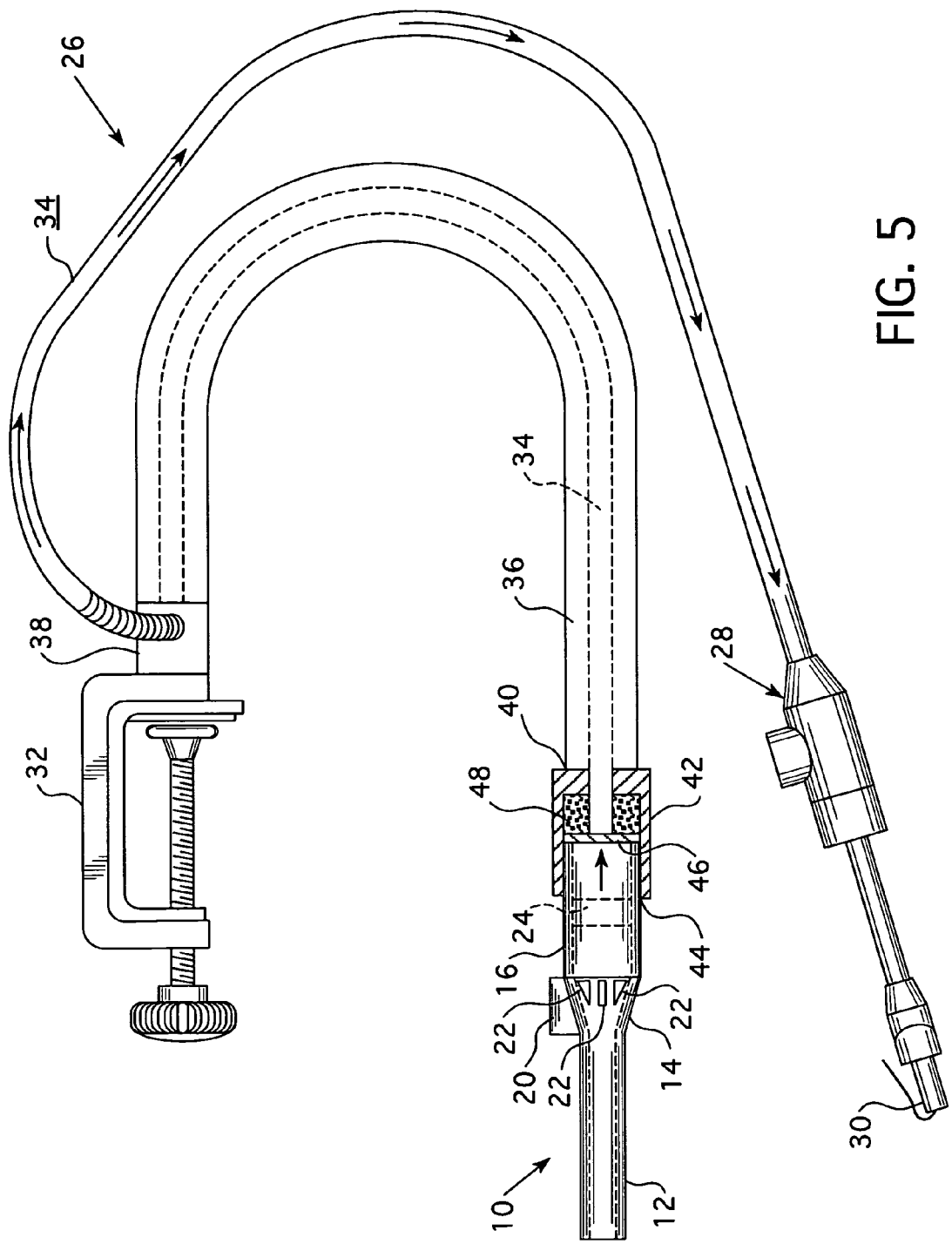
FIG. 5 is a perspective view of a breath controlled pneumatically actuated switching device comprising the mouth pipe and filter unit of FIG. 1 along with a connection member and plate shown in cross section.

FIGS. 1, 2, 3, 4 and 5 illustrate a mouth pipe and filter unit which may be used in a pneumatically actuated switching device such as that, for example, in FIG. 5, which is breath controlled by the user, e.g. a patient. With particular reference to FIGS. 1-4, the mouth pipe 10 comprises a first diameter section 12, a transition section 14 which is tapered, and an enlarged second diameter section 16. As best shown in FIG. 4, sections 12, 14 and 16 form a continuous airway 18 which extends entirely through sections 12, 14 and 16. The inner diameter of first diameter section 12 may range from about 3/16 inches to about 5/16 inches, and the outer diameter of first diameter section 12 may range from about 5/16 inches to about 7/16 inches. In an embodiment of the invention, the inner diameter of first diameter section 12 is about 3/16 inch and the outer diameter is about 5/16 inch (+ or −0.0005).

The inner diameter of enlarged second diameter section 16 of mouth pipe 10 may range from about 1/2 inch to about 15/16, and the outer diameter of enlarged second diameter section 16 may range from about 5/8 inch to about 11/16 inch. In an embodiment of the invention, the inner diameter of enlarged second diameter section 16 is about 1/2 inch and the outer diameter of enlarged second diameter section 14 is about 5/8 inch. The length of mouth pipe 10 may range from about 3 1/8 inches to about 3 2/8 inches. In an embodiment of the invention, the length of mouth pipe 10 is about 3 3/16 inches.

The mouth pipe 10 of FIGS. 1-5 is preferably a one-piece transparent member and has a projection 20 which is integrally formed along the transition section 14, and which mouth pipe 10 may either be formed through an extrusion process or an injection molding process. In an embodiment of the invention, mouth pipe 10 is made of a soft thermoplastic material, which may be selected from the group of materials consisting of polyvinyl chloride (PVC) and polyethylene, and/or combinations thereof. In an embodiment of the invention, mouth pipe 10 is made of PVC. As particularly shown in FIGS. 2 and 4, tapered transition section 14 of mouth pipe 10 includes a plurality of internal ribs 22. Ribs 22 are also formed in the fabrication of mouth pipe 10 and are strengthening elements for mouth pipe 10. Ribs 22 are arranged in a circular fashion around tapered transition section 14. In some embodiments, ribs 22 may not be provided; but mouth pipe 10 will still function according to its intended purpose.

Still referring to FIGS. 1-5, mouth pipe 10 further comprises a porous filter 24 shown in phantom in FIGS. 1, 2 and 3. Porous filter 24 is positioned within the enlarged second diameter section 16 of mouth pipe 10. In an embodiment of the invention, the outer diameter of porous filter 24 is about 1/2 inch depending on the size of the inner diameter of enlarged second diameter section 16. In any event, the outer diameter of porous filter 24 is such that porous filter 24 will be wedged within the inner diameter of enlarged second diameter section 16 of mouth pipe 10 so that it will be extremely difficult for a patient to blow into mouth pipe 10 and force porous filter 24 out of its position within enlarged second diameter section 16.

Porous filter 24, preferably, is made of a substantially rigid material. This material may be selected from a group of material consisting of polystyrene, plastic, and metal, e.g. brass and steel. In a preferred embodiment of the invention, the material of porous filter 24 is polystyrene. In an embodiment of the invention, the pore size of porous filter 24 may range from about 90 to 130 microns. In a preferred embodiment, the pore size is about 90 microns. The porous filter in general is a relatively small disc having a diameter ranging from about 1/4 inch to about 3/4 inch, preferably about 1/2 inch and a thickness ranging from about 3/16 to about 6/16 inch, preferably about 4/16 inch, depending on the dimensions of the mouth pipe 10.

Mouth pipe 10 and porous filter 24 are intended to be commercially sold and bought as a unit and used as such in a breath controlled device, such as, for example, the pneumatically actuated switching device of FIG. 5, which in turn, may be used, for example, in a patient call system. The breath controlled pneumatically actuated switching device 26 of FIG. 5 comprises a switch device 28 which is air activated and which may be an electrical switch device for generating an electrical signal for assistance. Switch device 28 comprises an electrical connection or plug 30 which is inserted into an outlet (not shown) near a patient's bed and which outlet is electrically connected to an alarm system in a nurse's station for assistance. An example of an electrical switch device which may be used as switch device 28 is disclosed in the above discussed U.S. Pat. No. 3,823,284 to Dwyer or in U.S. Pat. No. 7,449,646 to Wechtenhiser, et al. An example of a breath controlled pneumatically actuated switching device or monitoring system in which the mouth pipe 10 and porous filter 24 may be used as a unit is commercially available under the trademark BREATHCALL® which is manufactured by Dwyer Precision Products, Inc., Jacksonville, Fla., and which system is similar to that illustrated in FIG. 5.

Still referring to FIG. 5, breath controlled pneumatically actuated switching device 26 further comprises a clamp 32 for clamping or attaching device 26 to an object, such as, for example, a patient's bed. A conduit 36 is connected to clamp 32 via a connector member 38. Concentrically arranged within conduit 36 is an air tube 34 which extends out of connection member 38 via a coiled tubing 40, and which air tube 34 is connected to switch device 28. Conduit 36 may be made of coiled tubing and covered with a sturdy material, such as, for example rubber. This construction of conduit 36 allows conduit 36 with air tube 34 to be bent into a desired configuration for use of the pneumatically actuated switching device 26 by the patient while still protecting air tube 34. As shown by the arrows, air travels through air tube 34 and into switch device 28 for operation of switch device 28 in a taught in some of the aforesaid U.S. Patents, such as, for example, U.S. Pat. Nos. 3,823,285 and 7,449,646.

The opposite end 40 of conduit 36 is connected to a connector member 42, which has a vented open end 44 for receiving mouth pipe 10 with porous filter 24. Air tube 34 is connected to a plate 46 that is positioned within the vented open end 44 of connector member 42. Plate 46 is fixedly secured in connector member 42 via a substance, such as, for example, cement or an epoxy as indicated by reference numeral 48 which seals for air compression to contact plug 30 of switch device 28. Plate 46 is in the form of a disc and has a substantially small central aperture for allowing the blown air in mouth pipe 10 to enter air tube 34 as indicated by the arrow in mouth pipe 10 of FIG. 5.

Still referring to FIG. 5, the enlarged second diameter section 16 of mouth pipe 10 is forced or wedged into the vented open end 44 of connector member 42 and abuts against plate 46 to limit the extent of the insertion of mouth pipe 20 into connector member 42. The diameter of porous filter 24 is such that porous filter 24 is wedged within the inner walls of the enlarged second diameter section 16 of mouth pipe 10. However, if the air pressure is so forceful that it should cause filter 24 to become dislodged within mouth pipe 10, then plate 46 and substance 48 will limit movement of filter 24 within connector member 42.

For operation of the pneumatically actuated switching device 26 of FIG. 5, the contact for the switch device 28 to the alarm system in the nurse's system is normally open. Air is blown into mouth pipe 10, and travels into the small aperture (not shown) of plate 46 in connector member 42 and through air tube 34 and into switch device 28 to close the electrical contact to activate an alarm in the nurse's station.

Porous filter 24 is structured such that it aids in preventing bodily fluids such as saliva and/or blood of the patient from flowing into the air tube 34 and to switch device 28. Additionally, the diameter of porous filter 24 is sufficient that its edges fit tightly within the enlarged second diameter section 16 so that very little, if any, bodily fluids can flow around filter 24 and into air tube 34 and/or conduit 36 and the surrounding environment. This feature becomes important for sanitary reasons in that the pneumatically actuated switching device 26 can safely be used by other patients without very little concern of contamination. The mouth pipe 10 and porous filter 24 can be removed as a unit and replaced with a new clean unit for use by another patient.

The material of mouth pipe 10 is relatively flexible, for example, soft plastic, so that it can be slightly squeezed together and easily inserted into and removed from vented open end 44 of connector member 42 of FIG. 5. Additionally, this material of mouth pipe 10 will provide a frictional fit between connector member 42 and mouth pipe 10 to obtain and maintain an air tight seal between connector member 42, plate 46, and mouth pipe 10. The structure of mouth pipe 10, such as the transition section 14 between the first diameter section 12 and the enlarged second diameter section 16 and in some instances ribs 22, will retain the original shape of mouth pipe 10 so that air can be adequately blown into mouth pipe 10 and through air tube 34 for operation of device 26.

Referring again to FIGS. 1-4, projection 20 of mouth pipe 10 is provided for easy handling of mouth pipe 10 when mouth pipe 10 with porous filter 24 is being removed from and/or inserted into connector member 42 or when the patient inserts mouth pipe 10 into his or her mouth for operation of device 26.

Operation of mouth pipe 10 and pneumatically actuated switching device 26 is as follows: A patient places mouth pipe 10 into his or her mouth and blows air into the mouth pipe 10. The air is delivered into air tube 34 to operate switch device 28 for activation of an alarm. This electrical connection is generally maintained until a reset button on top the plug 30 or wall station is pushed down.

Mouth pipe 10 is made via a simple manufacturing process, such as, for example, an extrusion process or an injection molding process. Porous filter 24 is also made via a simple manufacturing process, such as, for example, a sheet molding process followed by a punching process. That is, a sheet of plastic material, such as, for example, polystyrene can be molded and the required shape of filter 24 can then be punched out of the molded sheet. The materials can be relatively inexpensive to obtain and produce. Both mouth pipe 10 and filter 24 can be mass produced, assembled and sold as a unit with several such units packaged together for mass marketing and for use in a breath controlled device, such as that illustrated in FIG. 5. The mouth pipe 10 and filter 24 as a unit are easily replaceable and removed from the device 26 for sanitation reasons so that the next person can use the device 26.

While the present invention has been described in connection with the embodiments of the various figures, it is to be understood that other similar embodiments may be used or modifications and additions may be made to the described embodiments for performing the same function of the present invention without deviating there from. Therefore, the present invention should not be limited to any single embodiment, but rather construed in breadth and scope in accordance with the recitation of the appended claims. Even though the mouth pipe unit of the invention has been disclosed relative to a pneumatically actuated switching device, it is to be appreciated that the mouth pipe unit of the invention can be used in other breath controlled devices.

What is claimed is:

1. In a pneumatically actuated switching device in a patient call system having a switch device for generating an electrical signal, a mouth pipe unit comprising:
   a mouth pipe in communication with the air tube for receiving air for activation of the switch device and comprised of a one-piece transparent member;
   a porous filter structured to be wedged in the mouthpiece and comprised of a relatively, rigid material, and having a pore size ranging from about 90 microns to about 130 microns;
   wherein the mouth pipe comprises a first diameter section, a transition section and an enlarged second diameter section in communication with the first diameter section and the transition section;
   wherein the first diameter section, the transition section, and the enlarged second diameter section comprise a continuous airway; and
   wherein the porous filter is wedged within the enlarged second diameter section of the mouth pipe.

2. In the pneumatically actuated switching device of claim 1, wherein the mouth pipe and the porous filter are structured as a unit.

3. In the pneumatically actuated switching device of claim 1, wherein the enlarged second diameter section includes an end section constructed to be in communication with the air tube for delivering air to the switch device.

4. In the pneumatically actuated switching device of claim 1, wherein the material of the mouth pipe is comprised of a soft plastic.

5. In the pneumatically actuated switching device of claim 1, wherein the material of the mouth pipe is comprised of polyvinyl chloride.

6. In the pneumatically actuated switching device of claim 1, wherein the porous filter comprises a pore size of about 90 microns; and wherein the material of the porous filter is comprised of polystyrene.

7. In the pneumatically actuated switching device of claim 1, wherein the mouth pipe further comprises an integral projection for grasping the mouth pipe.

8. In the pneumatically actuated switching device of claim 3, wherein the mouth pipe further comprises a plurality of ribs.

9. A mouth pipe unit for use in a device which is breath controlled, the mouth pipe unit comprising:
   a mouth pipe connectable to the device for operation of the device and comprised of a one-piece transparent member;
   a porous filter structured to be wedged in the mouth piece and comprised of a relatively rigid material and having pore size range from about 90 microns to about 130 microns;
   wherein the mouth pipe comprises a first diameter section, a transition section and an enlarged second diameter section in communication with the first diameter section and the transition section;
   wherein the first diameter section, the transition section, and the enlarged second diameter section comprise a continuous airway; and
   wherein the porous filter is wedged within the enlarged second diameter section of the mouth pipe.

10. The mouth pipe of claim 9, wherein the mouth pipe and the porous filter are structured as a unit.

11. The mouth pipe of claim 9, wherein the enlarged second diameter section includes an end section constructed to be inserted into a device for operation of the device.

12. The mouth pipe of claim 9, wherein the mouth pipe is comprised of a relatively soft plastic material.

13. The mouth pipe of claim 9, wherein the porous filter comprises a pore size of about 90 microns; and wherein the porous filter is comprised of polystyrene.

14. The mouth pipe of claim 9, wherein the mouth pipe further comprises an integral projection for grasping of the mouth pipe.

15. The mouth pipe of claim 9, wherein the mouth pipe further comprises a plurality of ribs.

* * * * *